(12) United States Patent
Huffmaster et al.

(10) Patent No.: US 9,351,851 B2
(45) Date of Patent: May 31, 2016

(54) DISC SPACE SIZING DEVICES AND METHODS FOR USING THE SAME

(71) Applicant: Benvenue Medical, Inc., Santa Clara, CA (US)

(72) Inventors: Andrew Huffmaster, Newark, CA (US); Patricia Hsin-Yi Ho, Redwood City, CA (US); Jeffrey L. Emery, Emerald Hills, CA (US); Laurent Schaller, Los Altos, CA (US)

(73) Assignee: Bevenue Medical, Inc., Santa Clara, CA (US)

( * ) Notice: Subject to any disclaimer, the term of this patent is extended or adjusted under 35 U.S.C. 154(b) by 430 days.

(21) Appl. No.: 13/804,847

(22) Filed: Mar. 14, 2013

(65) Prior Publication Data

US 2014/0135776 A1     May 15, 2014

Related U.S. Application Data

(60) Provisional application No. 61/724,416, filed on Nov. 9, 2012.

(51) Int. Cl.
  *A61F 2/46* (2006.01)
  *A61B 17/66* (2006.01)
  *A61F 2/44* (2006.01)

(52) U.S. Cl.
  CPC ............... *A61F 2/4657* (2013.01); *A61B 17/66* (2013.01); *A61F 2/4684* (2013.01); *A61F 2/442* (2013.01); *A61F 2/4455* (2013.01); *A61F 2002/4658* (2013.01)

(58) Field of Classification Search
  CPC ........... A61F 2/4657; A61F 2002/4633; A61F 2002/4658; A61B 17/66
  USPC ............................................................ 606/90
  See application file for complete search history.

(56) References Cited

U.S. PATENT DOCUMENTS

| | | | | |
|---|---|---|---|---|
| 2,002,021 | A | * | 5/1935 | Rouse ........................... 606/105 |
| 4,898,161 | A | * | 2/1990 | Grundei ......................... 606/105 |
| 5,540,696 | A | * | 7/1996 | Booth et al. ..................... 606/88 |

(Continued)

FOREIGN PATENT DOCUMENTS

WO   WO 03/024344 A1   3/2003
WO   WO 2011/150350     12/2011

OTHER PUBLICATIONS

Extended European Search Report for European Patent Appl'n. No. 11787510.4, dated Oct. 15, 2013.

(Continued)

*Primary Examiner* — Zade Coley
(74) *Attorney, Agent, or Firm* — Cook Alex Ltd.

(57) ABSTRACT

Devices and methods are provided for measuring and/or adjusting the distance between two opposing surfaces of a work space, such as two vertebral bodies separated by a disc space. A sizing device may include at least one distraction member, an actuator, and an actuator controller. The actuator controller is movable to move the actuator, with movement of the actuator changing the height dimension of the distraction member. The amount of movement of the actuator controller is generally linearly related to the change of the height dimension of the distraction member. The amount of expansion force applied by the distraction member is also generally linearly related to the amount of movement of the actuator controller.

20 Claims, 6 Drawing Sheets

(56) References Cited

U.S. PATENT DOCUMENTS

| | | | |
|---|---|---|---|
| 6,126,660 A * | 10/2000 | Dietz | 606/90 |
| 7,008,432 B2 * | 3/2006 | Schlapfer et al. | 606/90 |
| 7,771,432 B2 * | 8/2010 | Schwab et al. | 606/99 |
| 7,776,051 B2 * | 8/2010 | Colleran et al. | 606/105 |
| 8,128,662 B2 * | 3/2012 | Altarac et al. | 606/249 |
| 8,252,001 B2 | 8/2012 | Quirno et al. | |
| 8,377,070 B2 * | 2/2013 | Gauthier | 606/90 |
| 2001/0029377 A1 | 10/2001 | Aebi et al. | |
| 2003/0187453 A1 * | 10/2003 | Schlapfer et al. | 606/90 |
| 2003/0236520 A1 * | 12/2003 | Lim et al. | 606/61 |
| 2005/0080425 A1 * | 4/2005 | Bhatnagar et al. | 606/90 |
| 2005/0182416 A1 * | 8/2005 | Lim et al. | 606/90 |
| 2006/0052793 A1 * | 3/2006 | Heinz | A61B 17/025 |
| | | | 606/90 |
| 2006/0116689 A1 | 6/2006 | Albans | |
| 2007/0123903 A1 | 5/2007 | Raymond et al. | |
| 2007/0233143 A1 | 10/2007 | Josse et al. | |
| 2008/0287995 A1 * | 11/2008 | Gauthier | 606/246 |
| 2009/0005784 A1 * | 1/2009 | Blain | A61B 17/025 |
| | | | 606/90 |
| 2009/0198241 A1 * | 8/2009 | Phan | 606/90 |
| 2009/0198245 A1 * | 8/2009 | Phan | 606/99 |
| 2011/0112455 A1 * | 5/2011 | Rocklin | 602/32 |
| 2011/0172722 A1 | 7/2011 | Verhulst et al. | |
| 2012/0123426 A1 | 5/2012 | Quirno | |

OTHER PUBLICATIONS

International Search Report and Written Opinion for PCT Patent Appln. No. PCT/US2013/068906, dated Feb. 6, 2014.

* cited by examiner

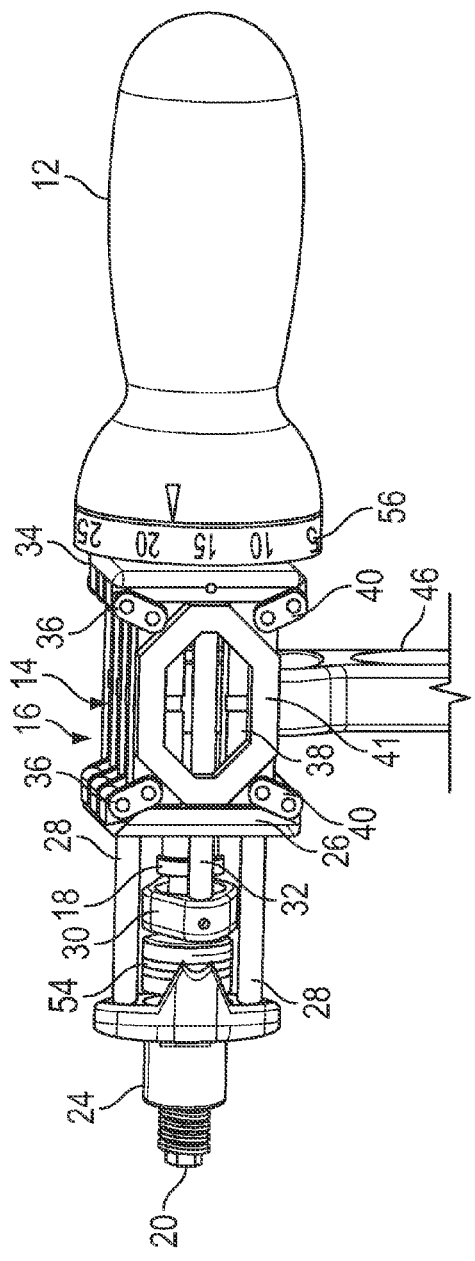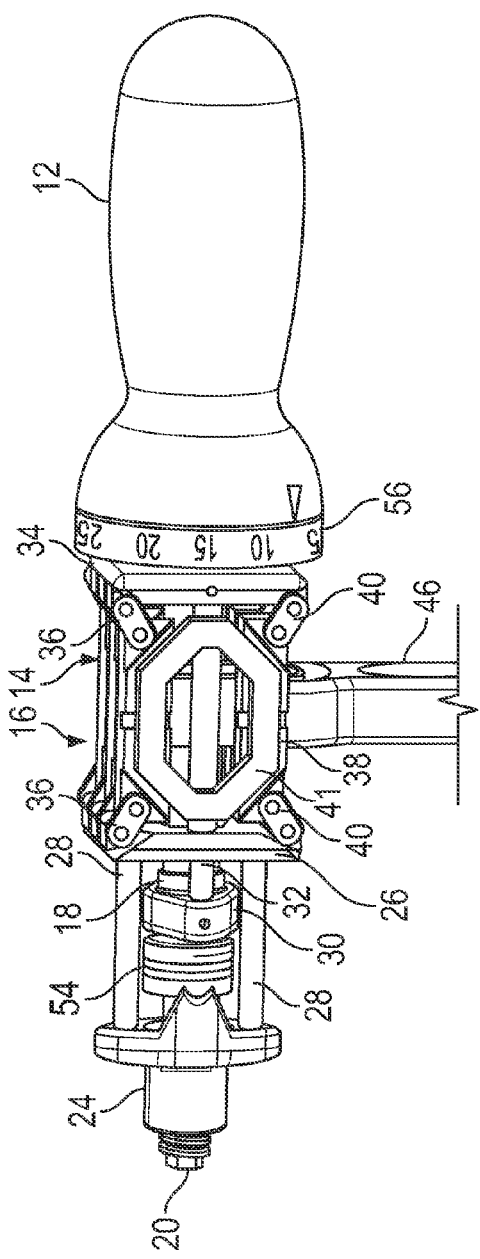

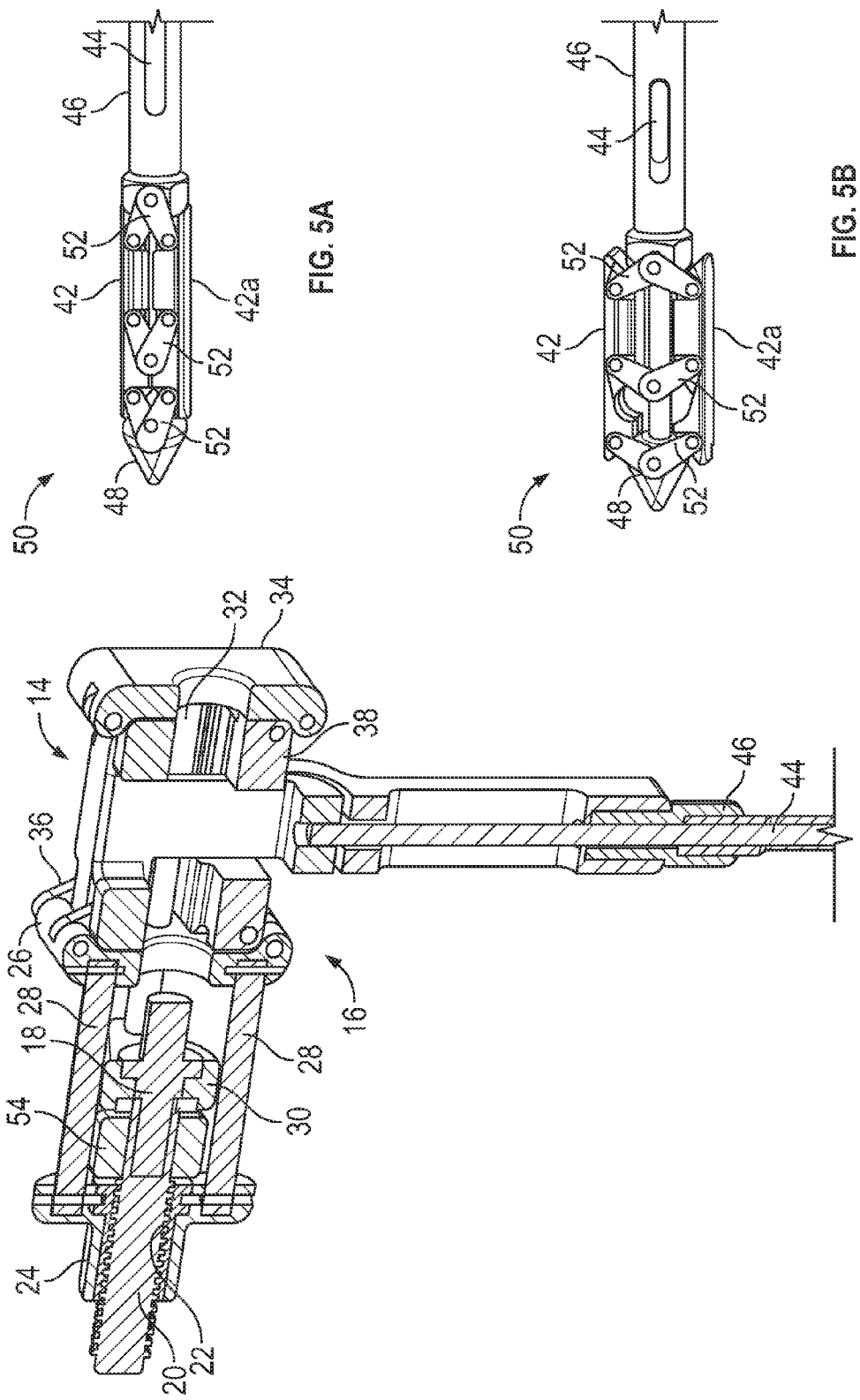

DISC SPACE SIZING DEVICES AND METHODS FOR USING THE SAME

CROSS-REFERENCE TO RELATED APPLICATIONS

This application claims the benefit of U.S. provisional patent application Ser. No. 61/724,416, filed on Nov. 9, 2012, which is incorporated herein by reference.

FIELD OF THE DISCLOSURE

The present subject matter relates to devices and methods for measuring and/or adjusting the spacing between two opposing surfaces, such as adjacent vertebral bodies.

DESCRIPTION OF RELATED ART

The spacing in the disc space between adjacent vertebral bodies may decrease for any of a number of reasons, including traumatic impacts and degenerative diseases. Improper spacing between adjacent vertebral bodies can lead to varying degrees of discomfort and/or pain and, if severe enough, may be reason for surgical correction of the spacing. One known method for surgical disc space sizing involves using traditional manual spreaders, which are often in the form shown in FIG. 1. Such known disc spreaders S are generally paddle-shaped, with one cross-sectional dimension H (referred to herein as its height) that is greater than another cross-sectional dimension W (referred to herein as its width). The distal end of the spreader S is inserted into the disc space in a flat orientation (i.e., with the plane of the spreader height H oriented parallel to the endplates of adjacent vertebral bodies) and then it is rotated 90° to re-orient the plane of the spreader height H perpendicular to the endplates. The height H of the spreader S is selected to equate to the proper separation between the adjacent vertebral bodies, such that the edges of the re-oriented spreader S contact the endplates and force proper spacing within the disc space. To accommodate different spacing situations, a set of spreaders is typically provided with a variety of heights H, which may range from 8 mm to 14 mm in 1 mm increments.

One disadvantage to such an approach is that the means for delivering the distal end of the spreader S to the disc area (e.g., a working cannula) must be large enough to accommodate the height H. Accordingly, a relatively large delivery cannula or means is required to accommodate the larger-sized spreaders. Larger spreaders also require a larger access site, resulting in greater surgical resection and more retraction of nerve roots and other surrounding structures. This can lead to the possibility of greater trauma, loss of blood, and pain, as well as potentially increased surgical and recovery time. Another disadvantage is that each spreader is appropriate for only one separation amount, so if a particular spreader is initially used and found to result in improper spacing, it must be removed and the process repeated with a spreader having a different width. The multiple tool exchanges inherent in such an iterative sizing procedure increases the risk of damaging nerve roots or other surrounding structures. Yet another possible disadvantage of the spreader S of FIG. 1 is that, as it is rotated between the endplates to achieve full height, the pressure applied by the rotating edge and, ultimately, the final edge of the spreader S are known to cause gouging and damage to the endplates. This damage can interfere with the fusion process and the placement of interbody devices into the disc space to facilitate fusion. Accordingly, it would be advantageous to provide a sizing device with contact surfaces that do not rotate into contact with the endplates, but instead are brought into contact therewith over a larger surface area.

Additional known spreaders are described in PCT publication no. WO/2011/150350, which is hereby incorporated herein by reference. The devices and methods described in PCT publication no. WO/2011/150350 represent an improvement to spreaders of the type illustrated in FIG. 1, but there remains room for improvement of the means and method for delivering and deploying such spreaders in the disc space.

SUMMARY

The subject matter of this application has number of aspects or features that may be employed as independent, standalone features or in combination with other or all of the aspects or features described herein. Without limiting this description to only the following aspects, or features the present subject matter include at least one or more of the following in addition to other aspects or features described herein.

In accordance with one aspect, a sizing device is provided for measuring and/or adjusting the spacing between two opposing surfaces. The sizing device includes at least one distraction member, an actuator, and an actuator controller. The distraction member is cooperatively associated with a distal end of the spacing device and is adapted for at least partial insertion into a space between two surfaces. The distraction member is also movable between a first configuration for insertion into the space in which the distraction member has a height dimension and a second configuration in which the distraction member has a larger height dimension for measuring and/or adjusting the spacing between the two surfaces. The actuator is associated with the distraction member and is movable to change the height dimension of the distraction member. The actuator controller is associated with the actuator and movable to move the actuator. The amount of movement of the actuator controller is generally linearly related to the change of the height dimension of the distraction member.

In accordance with another aspect, a method is provided for measuring and/or adjusting the spacing between two opposing surfaces. The method includes positioning at least one distraction member in a space between two surfaces. An actuator controller is moved to increase a height dimension of the at least one distraction member so as to bring the at least one distraction member into contact with one of the two surfaces. The amount of movement of the actuator controller is generally linearly related to the change of the height dimension of the at least one distraction member.

BRIEF DESCRIPTION OF THE DRAWINGS

FIG. 3A is a perspective view of a proximal portion of the sizing device of FIG. 2, in a first or unexpanded configuration;

FIG. 3B is a perspective view of a proximal portion of the sizing device of FIG. 2, in a second or expanded configuration;

FIG. 4 is a cross-sectional view of the proximal portion of FIG. 3, with an actuator controller thereof omitted for clarity;

FIG. 5A is a perspective view of a distal portion of the sizing device of FIG. 2, shown in a first or unexpanded configuration;

FIG. 5B is a perspective view of the distal portion of FIG. 5A, shown in a second or expanded configuration;

DESCRIPTION OF THE ILLUSTRATED EMBODIMENTS

The embodiments disclosed herein are for the purpose of providing the required description of the present subject matter. They are only exemplary, and may be embodied in various forms. Therefore, specific details disclosed herein are not to be interpreted as limiting the subject matter as defined in the accompanying claims.

Figure 1:
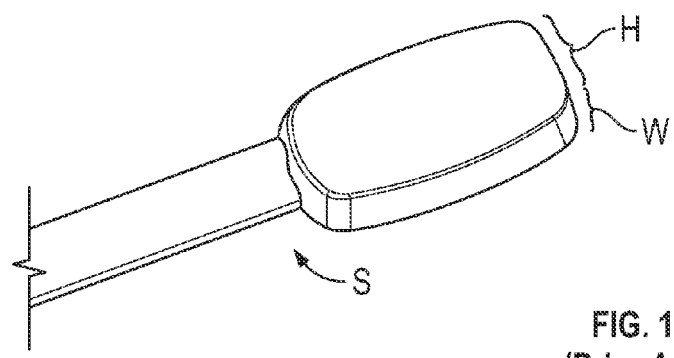
FIG. 1 is a perspective view of a known prior disc spreader.
Figure 2:
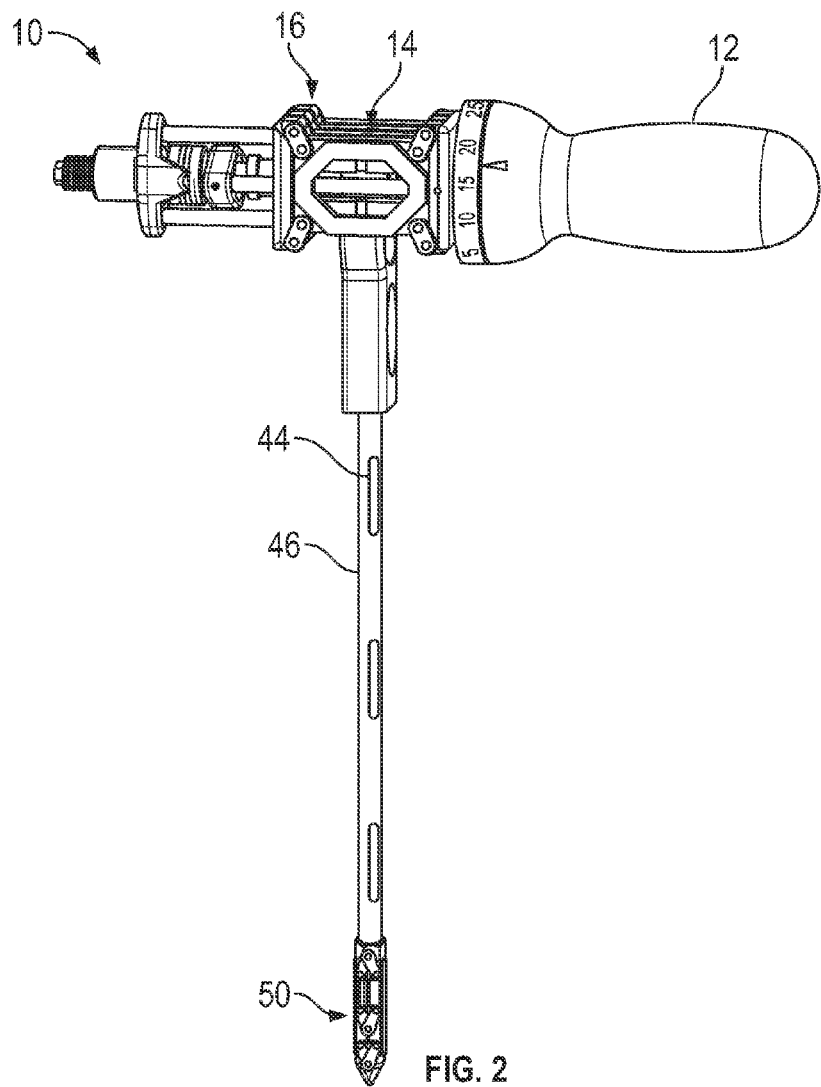
FIG. 2 is a perspective view of one embodiment of a sizing device according to an aspect of the present disclosure.

FIG. 2 shows one embodiment of a sizing device 10 according to the present disclosure. While the sizing device 10 of FIG. 2 may be particularly advantageous for measuring and/or adjusting the disc space separating adjacent vertebral bodies, it is within the scope of the present disclosure for the sizing device 10 to be used in other applications (including non-surgical applications). FIGS. 3A-4 show a proximal portion of the sizing device 10, while FIGS. 5A and 5B show a distal portion of the sizing device 10.

The proximal portion of the sizing device 10 includes a plurality of associated components. Among these components are an actuator controller 12 (FIGS. 3A and 3B), an actuator 14 (FIG. 4), and a proximal or controller-to-actuator linkage assembly or displacement converter 16 (FIGS. 3A-4). The proximal portion may include additional components, which will be described in greater detail herein. In FIG. 4, the actuator controller 12 is not illustrated, for the purpose of better showing the actuator 14 and the linkage assembly 16, but it should be understood that the actuator controller 12 may be configured to be removable from the remainder of the sizing device 10. This may be advantageous to allow for replacing one control mechanism (e.g., rotation of the actuator controller) with another control mechanism (e.g., sliding or translational movement of the actuator controller). In other embodiments, the actuator controller 12 may be permanently secured to the remainder of the sizing device 10. Other individual components of the sizing device 10 may also be removable and/or disposable and sterile. For example, all or a portion of the actuator 14 and/or the linkage assembly 16 may be readily detached by the user via a quick release lock so that an actuator and/or linkage assembly having a different configuration (e.g., an actuator and/or linkage assembly configured to separate two surfaces a greater extent that the original actuator and/or linkage assembly).

The actuator controller 12 and the actuator 14 are associated with each other via the proximal linkage assembly 16. The actuator controller 12 is configured to be manipulated by an operator during use of the sizing device 10, so it is preferably ergonomically designed. The exact configuration of the actuator controller 12 may vary, depending on the manner in which it is to be manipulated by an operator, but in one embodiment, it is configured to be rotated about an axis by the operator. In such an embodiment, it may be advantageous for the actuator controller 12 to be configured as an elongated handle that is rotated about its central axis (as shown in FIGS. 2-3B) or be otherwise configured to be gripped and rotated by an operator. Differently configured actuator controllers (e.g., ones that move by sliding or a similar translational movement) may also be employed without departing from the scope of the present disclosure.

The actuator controller 12 is associated with the proximal linkage assembly 16 such that movement of the actuator controller 12 also moves a portion of the proximal linkage assembly 16. Thus, in the illustrated embodiment, rotation of the actuator controller 12 also rotates a portion of the proximal linkage assembly 16. More particularly, in the illustrated embodiment, one end of the actuator controller 12 is fixedly or non-rotationally secured to a male hex attachment 18 (FIG. 4), such that rotation of the actuator controller 12 also rotates the hex attachment 18 of the proximal linkage assembly 16. In other embodiments, the actuator controller 12 may be connected to the proximal linkage assembly 16 by other means, but for embodiments in which the actuator controller 12 is rotated (as in the illustrated embodiment), it is preferred for the connection to be fixed or non-rotational, such that rotation of the actuator controller 12 will also rotate the portion of the proximal linkage assembly 16 to which it is connected or associated.

The hex attachment 18 may include external threads or, as in the illustrated embodiment, be fixedly or non-rotationally connected or secured to an externally threaded shaft or member 20 (FIG. 4). The external threads of the hex attachment 18 or the shaft 20 engage an internally threaded bore 22 of an end cap 24 positioned opposite the actuator controller 12. Rotating the hex attachment 18 and/or the shaft 20 moves the end cap 24 along the length of the hex attachment 18 or shaft 20 (if provided), such that rotation of the actuator controller 12 effectively causes translational movement of the end cap 24 (FIGS. 3A and 3B).

In the illustrated embodiment, the end cap 24 is rigidly connected to a first linkage fixture or carriage 26 by bolts 28 or the like, such that translational movement of the end cap 24 causes likewise translational movement of the fixture 26 (FIGS. 3A and 3B). Additional components may be provided to control movement of the first linkage fixture 26, such as a collar or disk 30 rotatably surrounding the hex attachment 18 and bolts or rods 32 extending therefrom (FIGS. 3A-4), for example. The rods 32 extend through bores or apertures of the first linkage fixture 26 (FIGS. 3B and 4) and are connected to a second linkage fixture or carriage 34 to help constrain the first linkage fixture 26 to substantially horizontal translational movement (in the orientation of FIGS. 2-4).

The first and second linkage fixtures 26 and 34 are pivotally connected to a proximal end portion of the actuator 14 by upper links 36, with the proximal end portion of the actuator 14 positioned between the fixtures 26 and 34. The first and second linkage fixtures 26 and 34 are also pivotally connected to a proximal end portion of the body 38 of the sizing device 10 by lower links 40. The outermost links 36 and 40 may be co-planar with or at least adjacent to a face plate 41, as shown in FIGS. 3A and 3B. The back side of the sizing device 10 is not illustrated, but similar face plates 41 may be applied to both the front and back sides of the sizing device 10. If provided, the face plates 41 may help to stabilize the proximal portion of the sizing device 10 and minimize non-perpendicular relative movement of the components that are to move perpendicularly with respect to each other, as will be described in greater detail herein. The illustrated face plate 41 is generally hexagonal or octagonal, but other shapes and configurations may be practiced without departing from the scope of the present disclosure.

Translational movement of the first linkage fixture 26 causes the upper and lower links 36 and 40 to pivot, with the upper and lower links 36 and 40 of the second linkage fixture 34 also pivoting as the first linkage fixture 26 moves toward (FIG. 3A) and away from (FIG. 3B) the second linkage fixture 34, which may be configured to be stationary. In the illustrated embodiment, there are four upper links 36 connecting each linkage fixture 26, 34 to the actuator 14 and four lower links 40 connecting each linkage fixture 26, 34 to the sizing device body 38 (i.e., a total of sixteen links). Such a configuration provides strength and stability to the linkage assembly 16, although other link configurations may also be employed without departing from the scope of the present disclosure. The links 36 and 40 may be retained by and articulate about cylindrical pins or other suitable retainers, which may be welded or otherwise secured to the junction between the actuator or body and the link.

As illustrated in FIG. 3B, movement of the first linkage fixture 26 away from the second linkage fixture 34 (in a horizontal direction in the orientation of FIGS. 2-4) causes the upper links 36 to pivot to translate the actuator 14 in an upward vertical direction (in the orientation of FIGS. 2-4), while the lower links 40 pivot to translate the sizing device body 38 in a downward vertical direction, thereby causing the actuator 14 and the sizing device body 38 to separate in a vertical direction. This results in expansion of a distal component of the sizing device 10, as shown in FIG. 5B, and as will be described in greater detail herein. On the other hand, as illustrated in FIG. 3A, movement of the first linkage fixture 26 toward the second linkage fixture 34 (in a horizontal direction in the orientation of FIGS. 2-4) causes the upper links 36 to pivot to translate the actuator 14 in a downward vertical direction, while the lower links 40 pivot to translate the sizing device body 38 in an upward vertical direction. This results in a distal component of the sizing device 10 collapsing or decreasing in height, as shown in FIG. 5A, and as will be described in greater detail herein.

Based on the foregoing, it will be seen that movement of the first linkage fixture 26 with respect to the second linkage fixture 34 (in either direction) causes movement of the actuator 14 and the sizing device body 38 in a substantially perpendicular direction. In other embodiments, the vertical movement of one of the actuator 14 and the sizing device body 38 may be restrained, such that only the other structure will move to effect relative vertical separation of the two structures, rather than both structures moving to effect such relative vertical separation. As noted above and as will be described in greater detail herein, relative vertical translational movement of the actuator 14 changes the height dimension of one or more contact plates or distraction members 42, 42a at the distal end of the sizing device 10 (FIGS. 5A and 5B) for measuring and/or adjusting the spacing between adjacent vertebral bodies.

The actuator 14 of the illustrated embodiment includes (either integrally formed with or separate from the proximal end portion) a shaft or rod 44 (FIG. 4). According to different embodiments, the rod 44 may be configured as a wire or cable, particularly in embodiments wherein a distal distraction component of the sizing device 10 is provided with a curved configuration, as further described herein. Depending on the intended use, the size and material composition of the rod 44 may vary widely, but in one embodiment that may be particularly advantageous for use in the vertebral disc space, the rod 44 has an outer diameter of approximately 6 mm and is manufactured of a 17-4 grade stainless steel. Other suitable materials (e.g., metallic or polymeric materials) may also be used without departing from the scope of the present disclosure.

The rod 44 of the actuator 14 may be referred to herein as the inner shaft or rod, because it may be positioned within an outer shaft 46. The outer shaft 46 may be integrally formed with or otherwise rigidly connected to the sizing device body 38, with a hollow interior that is sufficiently sized to allow coaxial translation movement of the inner rod 44. The outer shaft 46, if provided, may help to maintain the relative position and proper alignment of the inner rod 44 during use, as well as helping in the opening and closing of distal distraction members of the sizing device 10. In other embodiments, the functions of the outer shaft 46 and the inner rod 44 may be reversed, with the inner rod 44 supporting an outer shaft 46 associated with the actuator 14. As shown, the generally wall of the outer shaft 46 may include one or more slots or openings through which the inner rod 46 may be seen or accessed. Such slots may facilitate cleaning of the sizing device 10, if it is to be reused.

A distal end 48 of the inner rod 44 (or a separate component secured to the end of the inner rod 44) extends outside of the distal end of the outer shaft 46 (FIGS. 5A and 5B), where it is connected to at least one distraction member 42, 42a of an adjustable sizing paddle 50. In the illustrated embodiment, the distal end 48 of the inner rod 44 is ramped or angle or otherwise configured to have a height that increases proximally from its distal end. Such a configuration provides a distal "bullet" nose, which facilitates entry into spaces (e.g., tight or collapsed disc spaces) when the adjustable sizing paddle 50 is in the unexpanded configuration of FIG. 5A. This feature also reduces risk of catching or snagging nearby surfaces (e.g., soft tissue). Other configurations may also be employed without departing from the scope of the present disclosure.

In the illustrated embodiment, the distal end of the inner rod 48 of the actuator 14 is hingedly connected via links 52 to a pair of distraction members 42 and 42a, with the distal end 48 of the inner rod 44 of the actuator 14 being configured for movement between the distraction members 42 and 42a. FIGS. 5A and 5B show a preferred embodiment, in which six sets of link pairs (which are symmetrical between the "left" and "right" sides) enable the lifting of the contact plates or distraction members. These link pairs are optimally positioned to maximize the strength of the adjustable sizing paddle 50. The links 52 may be retained by and articulate about cylindrical pins, which may be welded at the junction between the pin and link. To minimize the types of links used in the adjustable sizing paddle 50, the left hand distal and middle link pairs may be identical to the right hand proximal link pair, while the proximal left link pair may be identical to the right distal and middle link pairs.

In other embodiments, the adjustable sizing paddle may include fewer or more distraction members than are shown in the illustrated embodiment. Preferably, there are at least two distraction members positioned on opposite sides of the actuator, such that one of the distraction members may provide a suitable contact surface for one of the surfaces to be distracted and the other distraction member may provide a suitable contact surface for the other surface to be distracted. Further, it is also within the scope of the present disclosure for the actuator to be connected to the distraction member(s) of the adjustable sizing paddle in a different manner than what is shown in the illustrated embodiment. For example, it may be preferable for the distraction members to be hingedly or otherwise movably connected to the actuator, but it is also within the scope of the present disclosure for at least one of the distraction members to be fixedly secured to the actuator or otherwise associated with the actuator in such a way that the height dimension of the distraction member does not change upon movement of the actuator.

In the illustrated embodiment, the portions of the distraction members 42 and 42a that contact the surfaces to be distracted (i.e., the upper portion or face of the upper distraction member 42 and the lower portion or face of the lower distraction member 42a) are substantially parallel, which may be advantageous for separating parallel surfaces, but other configurations may also be employed without departing from the scope of the present disclosure. For example, when the surfaces to be distracted or separated by the sizing device 10 are non-parallel (e.g., when a sizing device according to the present disclosure is used in Iordotic intradiscal spaces), it may be advantageous for the contact surfaces of the distraction members 42 and 42a to be substantially non-parallel. In the exemplary case of a sizing device used in a Iordotic intradiscal space, it may be preferred for the contact surfaces of the distraction members to be separated from each other by different distances at their proximal and distal ends. For example, the distal separation between the contact surfaces of the distraction members may be greater than the separation therebetween at a more proximal portion, with the separation therebetween increasing from the distal to the proximal portions. The angle from anterior to posterior is typically between approximately 5° and 15° in the adult lumbar spine at the level L5-S1. Thus, a similar angle could be incorporated into the distraction members of the sizing device.

Proximal relative movement of the actuator 14 (i.e., upward movement in the orientation of FIGS. 2-4 or left-to-right movement in the orientation of FIGS. 5A and 5B) causes the links 52 to pivot, with the upper links moving the upper distraction member 42 outwardly from the unexpanded configuration of FIG. 5A to the expanded configuration of FIG. 5B. The distal end of the outer shaft 46 may be configured to butt against the proximal end of the distraction member(s) 42 and 42a to promote pivotal movement of the links 52 upon proximal movement of the actuator rod 44. Such outward movement of a distraction member is referred to herein as an increase in the height dimension of the distraction member. As used herein, the term "height dimension" (when used in reference to an individual distraction member) refers to the distance between the distraction member and a reference point (e.g., the central axis of the actuator rod), such that the distraction members have a minimum height dimension in the configuration of FIG. 5A and a larger height dimension in the configuration of FIG. 5B.

Similarly, proximal relative movement of the actuator 14 causes the lower links 52 to move the lower distraction member 42a outwardly from the unexpanded configuration of FIG. 5A to the expanded configuration of FIG. 5B. For adjustable sizing paddles having opposed distraction members (as in the illustrated embodiment), the term "height dimension" may also be used in reference to the adjustable sizing paddle itself, in which case the term refers to the distance between the distraction members. Thus, when the height dimension of the individual distraction members of a dual-distraction member adjustable sizing paddle (as in the illustrated embodiment) is measured with respect to the central axis of the actuator rod 44, it will be seen that the height dimension of the adjustable sizing paddle is equal to the sum of the height dimensions of the distraction members. This is a preferred configuration and relationship between the distraction members and the adjustable sizing paddle, but other configurations and relationships may also be practiced without departing from the scope of the present disclosure.

In use, the distraction member(s) 42 and 42a and/or the adjustable sizing paddle 50 are positioned in the work space (e.g., a vertebral disc space) with a minimum height dimension (FIG. 5A) or a relatively small height dimension. The height dimension of the distraction member(s) 42 and 42a and/or adjustable sizing paddle 50 is increased (as described above) to bring the distraction member(s) 42 and 42a into contact with the surfaces to be distracted (e.g., opposing vertebral bodies). After making contact with the surfaces to be distracted, the height dimension is further increased to increase the separation between the surfaces.

After the surfaces have been suitably distracted and any other accompanying operation is performed in the work space, the height dimension of the distraction member(s) 42 and 42 and/or the adjustable sizing paddle 50 is decreased to disengage the opposing surfaces of the work space. This is achieved by distal relative movement of the actuator 14 (i.e., downward movement in the orientation of FIGS. 2-4 or right-to-left movement in the orientation of FIGS. 5A and 5B), the links 52 pivot so as to cause the distraction members 42 and 42a to move inwardly from the expanded configuration of FIG. 5B toward the unexpanded configuration of FIG. 5A. The configuration in which the distraction members and the adjustable sizing paddle have a minimum height dimension for insertion into a work space is referred to herein as the "first configuration," while the configuration in which the distraction members and the adjustable sizing paddle having a maximum height dimension is referred to herein as the "second configuration." The height dimension of the distraction members and the adjustable sizing paddle may be infinitely or discretely adjustable between the first and second configurations, such that there may be either an infinite or a discrete number of intermediate positions between the first and second configurations.

The distraction members 42 and 42a may be variously configured, but in a preferred embodiment, they are configured to provide "nests" to accommodate the links 52 so as to minimize the insertion profile of the adjustable sizing paddle 50 in the first configuration of FIG. 5A. The contours of the distraction members 42 and 42a that allow for "nesting" of the links 52 are best seen in FIG. 5B, with side walls of the distraction members 42 and 42a (i.e., the surfaces of the distraction members 42 and 42a to which the links 52 are secured, rather than the portions of the distraction members 42 and 42a that contact the surfaces to be separated) being contoured to allow the side walls of the distraction members 42 and 42a to fully approach and contact one another without interference from the links 52 (as in FIG. 5A). The size of the adjustable sizing paddle 50 may vary widely, depending on the nature of the surfaces to be separated, but in a preferred embodiment that may be particularly advantageous for use in a vertebral disc space, the distraction members 42 and 42a and links 52 are configured to allow for a minimum profile (FIG. 5A) of the adjustable sizing paddle 50 measuring 7×7 mm in cross-section, with the adjustable sizing paddle 50 being able to at least 13 mm in height. The length of the adjustable sizing paddle 50 may also vary, but in one embodiment that may be particularly advantageous for use in a vertebral disc space, the adjustable sizing paddle 50 has a length of approximately 30 mm, which accommodates the expected anterior-posterior distance seen in most adult lumbar discs. It should be understood that, while the illustrated adjustable sizing paddle 50 is provided as a substantially linear or straight component, it is also within the scope of the present disclosure for the paddle 50 to be generally non-linear, with a slight curve to facilitate distraction across the mid-line of a vertebral body, as described in greater detail below with respect to other embodiments of the present disclosure.

The adjustable sizing paddle 50 (and other components of the sizing device 10) may be constructed out of a variety of materials. In a preferred embodiment, which may be particularly advantageous for use in surgical applications, the adjustable sizing paddle 50 and other components of the sizing device 10 are constructed out of surgical grade stainless steel, such as the 17-4 alloy. Such a material composition may render the adjustable sizing paddle 50 sufficiently strong so as to withstand reaction forces (e.g., vertebral endplate reaction forces) of up to 300 pounds, which may be possible in cases of severely collapsed and diseased disc spaces. While it may be preferred for the sizing device 10 to be a reusable instrument and constructed out of materials, such as stainless steel, than can withstand the cleaning and sterilization procedures used by hospitals or the like, it is also within the scope of the present disclosure for the sizing device 10 to be disposable. Rather than using machined or forged steel, high strength polymers which can be readily molded could be used for components which are subject to high stresses, such as the links 52 of the adjustable sizing paddle 50, to reduce the cost of the sizing device 10.

As described above, movement of the actuator controller 12 effectively moves the actuator 14, meaning that movement of the actuator controller 12 (rotational movement in the illustrated embodiment) ultimately changes the height dimension of the distraction members 42 and 42a and the adjustable sizing paddle 50. Preferably, as in the illustrated embodiment, the amount of movement of the actuator controller 12 is generally linearly related to the change of the height dimension of the distraction members 42 and 42a and the adjustable sizing paddle 50. By way of example, for a rotary actuator controller (as in the illustrated embodiment), this means that rotating the actuator controller a particular amount will always result in the same change in the height dimension of the distraction members and the adjustable sizing paddle (up to the maximum and minimum height dimensions), regardless of the current height dimension. In one example, rotating the actuator controller 12 approximately 270° about its rotational axis increases the height dimension of the adjustable sizing paddle 50 by 1 mm regardless of the current height dimension of the adjustable sizing paddle 50 (up to the maximum height dimension of the adjustable sizing paddle 50, at which point the actuator controller 12 may be configured to cease further clockwise rotation or to "clutch out" and slip without further expanding the adjustable sizing paddle 50). In this same example, rotation of the actuator controller 12 approximately 270° in the opposite direction about its rotational axis decreases the height dimension of the adjustable sizing paddle 50 by 1 mm regardless of the current height of the adjustable sizing paddle 50 (up to the minimum height dimension of the adjustable sizing paddle 50, at which point the actuator controller 12 may be configured to cease further counter-clockwise rotation or to "clutch out" and slip without further contraction of the adjustable sizing paddle 50).

In an alternative embodiment, the force developed in the sizing device 10 may be limited by constructing all or a portion of the actuator rod 44 from a superelastic material (e.g., Nitinol). By such a configuration, the actuation force to expand the adjustable sizing paddle 50 may be progressively developed by the proximal handle assembly up until the "superelastic" plateau of the material is reached. Thereafter, no additional force (or displacement) will be generated in the adjustable sizing paddle 50 because the force-length behavior of the superelastic material will flatten out as it transitions from a linear force-length relationship to a more flat relationship. Thus, as the actuator controller 12 keeps turning, no additional vertical displacement would occur at the adjustable sizing paddle 50. The force at which this occurs may be controlled by a variety of factors, including the cross-sectional geometry and length of the actuator rod 44.

In addition to the components described above, the sizing device 10 may include additional components. For example, FIGS. 2-4 illustrate a sizing device 10 having a readout indicator feature that conveys to the user the height dimension of the distraction member(s) 42, 42a and/or the adjustable sizing paddle 50. In the illustrated embodiment, the readout indicator feature comprises a generally annular or tubular member 54. The readout indicator 54 of FIGS. 2-4 includes a central opening or aperture through which the externally threaded shaft 20 and/or a portion of the hex attachment 18 extends. The readout indicator 54 may be fixedly or non-rotationally associated with the shaft 20 and/or the hex attachment 18, such that the readout indicator 54 rotates with the shaft 20 and/or the hex attachment 18. The outer surface of the illustrated readout indicator 54 includes markings, such as numerical markings that indicate to the user the current height dimension of the distraction member(s) 42, 42a and/or the adjustable sizing paddle 50 (e.g., markings from 7 to 13 mm in 1 mm increments spaced along at least a portion of the outer surface of the readout indicator 54). Other configurations of a readout indicator may also be employed without departing from the scope of the present disclosure. For example, the actuator controller 12 itself may include markings that are indicative of the current height dimension of the distraction member(s) 42, 42a and/or the adjustable sizing paddle 50, thereby providing a combined or integrated actuator controller and readout indicator.

As described above, one advantage of sizing devices according to the present disclosure is that movement of the actuator controller results in a generally uniform change in the height dimension of the distraction member(s) and/or the adjustable sizing paddle (i.e., there is a generally linear relationship between the movement of the actuator controller and the change in height dimension of the distraction member(s) and/or the adjustable sizing paddle). A related advantage and feature is that an expanding distraction member or adjustable sizing paddle will exert a generally uniform outward force upon movement of the actuator controller, in contrast to known devices, which may be height dependent (i.e., they exert a varying outward force depending on the distance between the surfaces to be distracted). To take advantage of this feature, the sizing device may be provided with a force measurement feature and clutch assembly. In the illustrated embodiment, the actuator controller 12 comprises a torque handle with an adjustable or fixed clutch point configured to deliver between 8 and 32 inch-pounds of torque, such as an adjustable torque handle or wrench of the type manufactured by Tecomet of Wilmington, Mass., but any other torque-limiting deployment device that is suitable for orthopedic use may also be employed without departing from the scope of the present disclosure. The maximum reaction force (i.e., the force exerted on the distraction member(s) and/or the adjustable sizing paddle by opposing vertebral bodies or any other two surfaces to be separated by the sizing device) may be selected prior to use of the sizing device. If the clutch point is adjustable, then the maximum reaction force may be selected by adjusting the corresponding assembly; otherwise, if the clutch point it fixed, the user may select a sizing device having the desired fixed clutch point. In the illustrated embodiment, the actuator controller 12 includes an adjustable clutch point, which is embodied as a disk 56 having markings that indicate a maximum reaction force (e.g., a numerical value in inch-pounds). Another indicator (e.g., an arrow or line) is located on a portion of the actuator controller 12 that is rotatable or adjustable with respect to the disk 56, such that the indicator may be used to indicate the maximum reaction force by rotating it to the corresponding mark on the disk 56.

By selecting a maximum reaction force, the risk of causing damage to a disc space or other work space by applying excessive spreading force with the sizing device may be decreased. As the actuator controller is moved to expand and increase the height dimension of the distraction member(s) and/or the adjustable sizing paddle, the reaction force applied thereto by the disc space or other work space will increase as the two opposing surfaces are pressed farther apart. When the maximum reaction force is reached, the clutch assembly will "clutch out" to prevent further expansion of the distraction member(s) and/or the adjustable sizing paddle. In the illustrated embodiment, "clutching out" refers to the actuator controller being rotated in the expansion direction without causing the distraction member(s) and/or the adjustable sizing paddle to expand or increase in height dimension. In the case of an adjustable torque handle, the user could adjust the maximum reaction force from one value to a higher value so as to slowly "walk up" the applied load until a predefined value is reached.

In the illustrated embodiment of FIGS. 2-5B, the actuator controller 12 is configured for rotational movement, while the actuator 14 is configured for translational movement. More particularly, the actuator controller 12 is rotatable about an axis oriented at an angle with respect to the direction of movement of the actuator 14. In the illustrated embodiment, the actuator controller 12 is rotatable about an axis that is substantially perpendicular to the direction of movement of the actuator 14, but it is also within the scope of the present disclosure for there to be different relationships between the movements of the actuator controller and the actuator. For example, it should be understood that the rotary handle of FIGS. 2-5B may be replaced with a non-rotary device, such as a sliding or translating actuator controller that slides or otherwise moves in a direction at an angle or perpendicular to the direction of movement of the actuator, such as by sliding in a direction parallel to the rotational axis of the illustrated actuator controller 12. In such an embodiment, the actuator controller could move the first linkage fixture 26 toward and away from the second linkage fixture 34 by translating or sliding in a left-to-right or right-to-left direction (in the orientation of FIGS. 2-4), thereby moving the actuator 14, as described above. In other embodiments, such as those illustrated in FIGS. 6A-8B, the actuator controller may be configured to rotate about an axis parallel to the direction of movement of the actuator and/or to translate in substantially the same direction as the actuator to move the actuator.

Figure 6A:
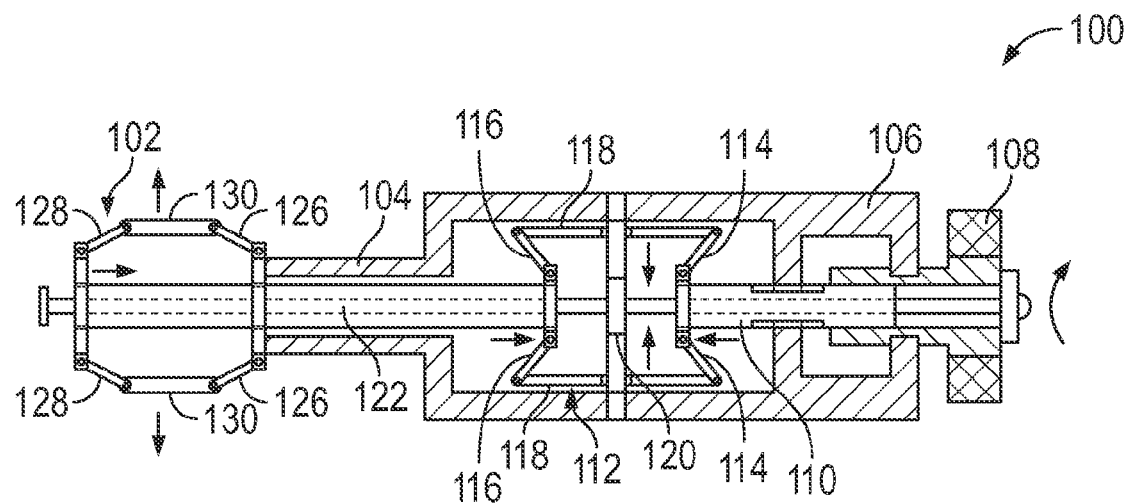
FIG. 6A is a cross-sectional view of another embodiment of a sizing device according to an aspect of the present disclosure, shown in a first or unexpanded configuration.
Figure 6B:
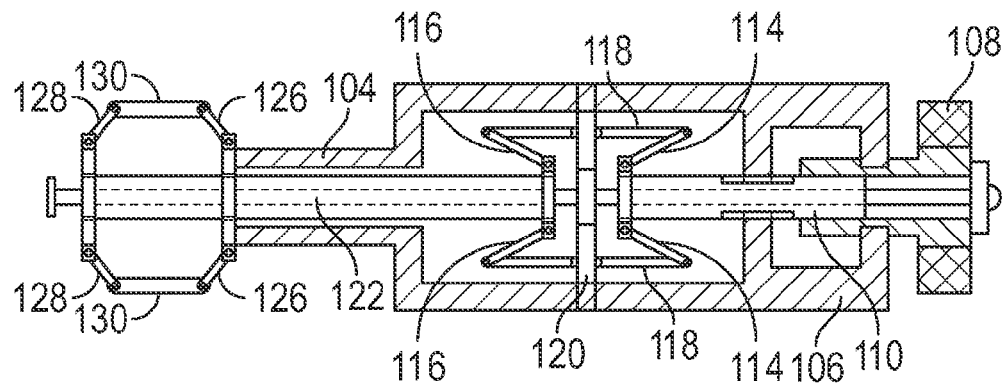
FIG. 6B is a cross-sectional view of the sizing device of FIG. 6A, shown in a second or expanded configuration.

In the embodiment of FIGS. 6A and 6B, an in-line sizing device 100 provides a linear movement relationship between the amount that the proximal actuator controller (such as the rotation of a rotary handle) is moved and the change in the expansion or contraction of the distal distraction members and/or the adjustable sizing paddle. To achieve this relationship, the illustrated sizing device 100 employs a pair of scissor linkage assemblies that act in opposite directions. More specifically, FIGS. 6A and 6B show the sizing device 100 as having a distal sizing/distraction assembly or adjustable sizing paddle 102 comprising a distal scissor linkage assembly, with a shaft 104 extending proximally thereof.

The proximal end portion of the sizing device 100 includes a housing 106 that has a actuator controller, such as a rotary knob 108, mounted at one end thereof. The illustrated knob 108 is threadedly attached to one end of an axially movable shaft 110. The other end of the shaft 110 is attached to one side of a proximal scissors linkage assembly 112. The proximal linkage assembly 112 may include a pair of opposed proximal links 114, a pair of opposed distal links 116, and a pair of outer links 118 that connect the proximal and distal links 114 and 116. The proximal linkage assembly 112 is mounted within the housing 106 and held in a generally fixed axial position by guide 120. When the handle or knob 108 is turned, the threaded screw action between the knob 108 and the shaft 110 causes the shaft 110 to move axially, either pushing or pulling on the proximal linkage assembly 112, depending on the direction of shaft movement. As illustrated in FIG. 6A, if the shaft 110 exerts a pushing force on the proximal links 114 (i.e., by moving in the right-to-left direction in the orientation of FIGS. 6A and 6B), it causes the outer links 118 to move closer together (as seen in FIG. 6B) and mechanically results in the distal links 116 exerting a proximally directed (i.e., left-to-right) pulling force on an axially movable shaft or actuator 122 that extends through the surrounding fixed shaft 104. In contrast, if the shaft 110 exerts a pulling force on the proximal on the proximal links 114 (i.e., by moving in the left-to-right direction in the orientation of FIGS. 6A and 6B), it causes the outer links 118 to move apart and mechanically results in the distal links 116 a distally directed (i.e., right-to-left) pushing force on the actuator 122.

The distal scissor linkage assembly or adjustable sizing paddle 102 is of similar construction to the proximal scissor linkage assembly 112 described above and is attached at the end of the shaft 104. The distal linkage assembly 102 has a pair of proximal links 126, a pair of distal links 128, and a pair of outer links 130 that define distraction members. The actuator 122 that is moved by the proximal linkage assembly 112 extends through the distal linkage assembly 102 and engages the distal links 128, such that axial force exerted in a distal direction tends to force the outer links 130 apart and axial force exerted in a proximal direction (as in FIG. 6A) tends to pull the outer links 130 together. The consequence of this arrangement is that the linkage assemblies 112 and 102 act in opposite directions. As illustrated in FIG. 6A, contraction of the proximal linkage assembly 112 when the shaft 110 is pushed in a distal direction (e.g., by clockwise rotation of the knob 108) results in pulling the actuator 122 in a proximal direction which acts on the distal linkage assembly 102 to move it from a first or unexpanded configuration (FIG. 6A) to a second or expanded configuration in which the outer links 130 are farther apart (FIG. 6B). By such an operation, it will be seen that the height dimension of the adjustable sizing paddle 102 (i.e., the distance between the outer links or distraction members 130) has been increased.

When the shaft 110 is pulled in a proximal direction (e.g. by counter-clockwise rotation of the knob 108), the proximal linkage assembly 112 expands (e.g., from the configuration of FIG. 6B to the configuration of FIG. 6A) and exerts a distal pushing force on actuator 122. The actuator 122 pushes the distal links 128 of the distal linkage assembly or adjustable sizing paddle 102 and causes contraction of the outer links or distraction members 130, thereby effectively decreasing the height dimension of the adjustable sizing paddle 102. It should be understood that the illustrated configuration is merely exemplary, and it is within the scope of the present disclosure for the orientations of the proximal and distal linkage assemblies to be reversed, although the directions of knob rotation and shaft movement may also be reversed. In any event, the series scissor linkage assembly mechanical connection between the knob 108 and the distal linkage assembly or adjustable sizing paddle 102 is linear, such that the rotation of the knob 108 a selected amount changes the distance between the outer links or distraction members 130 in a linearly predictable manner, so that the amount or degree of knob rotation is linearly proportional to the change in the height dimension of the distraction members 130 and/or the adjustable sizing paddle 102.

It is within the scope of the present disclosure to make any of a number of variations to the sizing device 100 of FIGS. 6A and 6B, including one or more of the variations described above with respect to the embodiment of FIGS. 2-5B. For example, the rotary actuator controller 108 may be replaced by an actuator controller that moves differently, such as by sliding or translating in a direction generally parallel to the movement of the actuator 122, or the distraction members 130 may be provided with non-parallel outer contact surfaces or there may be only one movable distraction member 130. In another example, the adjustable sizing paddle 50 of FIGS. 5A and 5B may be coupled to the proximal handle mechanism of the sizing device 100 of FIGS. 6A and 6B for a larger contact surface.

Figure 7A:
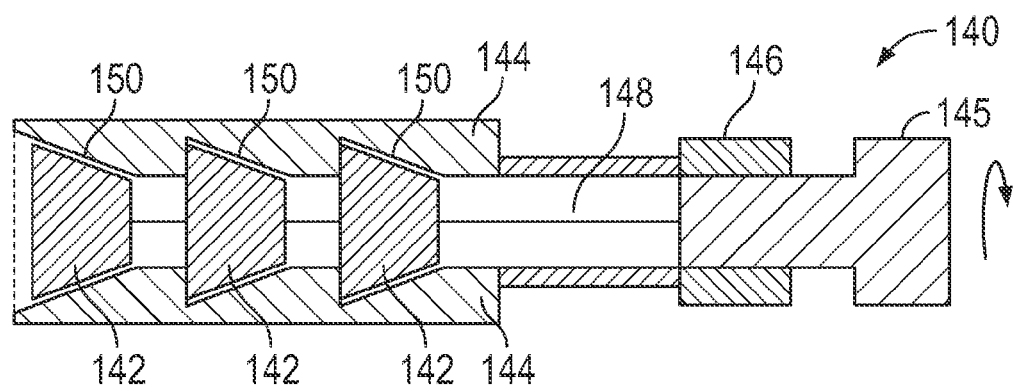
FIG. 7A is a cross-sectional view of another embodiment of a sizing device according to an aspect of the present disclosure, shown in a first or unexpanded configuration.
Figure 7B:
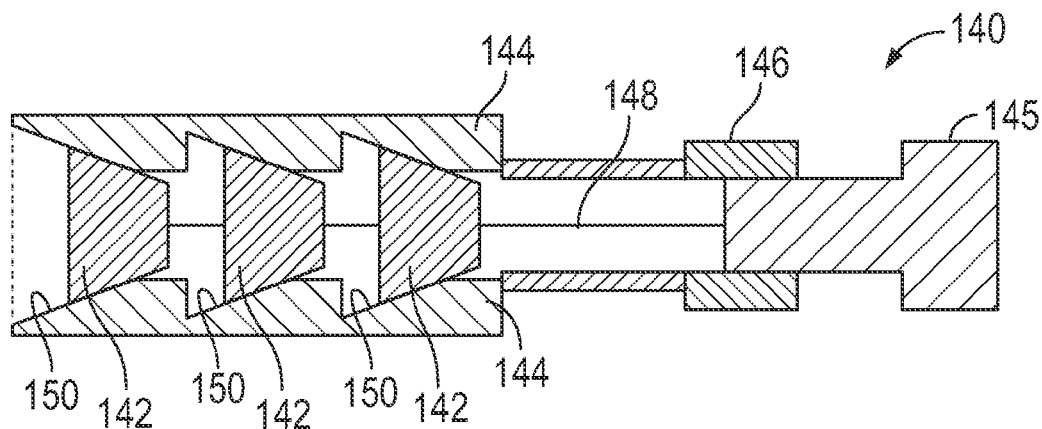
FIG. 7B is a cross-sectional view of the sizing device of FIG. 7A, shown in a second or expanded configuration.

FIGS. 7A and 7B show another embodiment or alternative in which an in-line or straight mechanical arrangement is provided, in contrast to the right angle arrangement of FIGS. 2-5B. In this embodiment, the sizing device 140 employs one or more wedge-shaped spacers or spreaders 142 of an actuator that are linearly movable to adjust the spacing between opposed sizing or distraction members or surfaces 144 (which collectively define an adjustable sizing paddle, as in the above-described embodiments).

The sizing device 140 is illustrated with an actuator controller, such as a rotary knob or handle 145, that is rotatably mounted at one end of a housing 146 and threadedly engaged with a push-pull shaft or actuator 148 that extends through the housing 146 to one or more of the wedge-shaped spacers or spreaders 142. In the illustrated embodiment, three spacers 142 are secured to the actuator 148, with each one being seated within a wedge-shaped cavity defined between inner surfaces 150 of the distraction members 144 (FIG. 7A). The distraction members 144 are preferably fixed against axial movement relative to the spacers 142 so that proximal relative movement of the actuator shaft 148 causes the spacers 142 to bear against the inclined inner surfaces 150 of the distraction members 144 to expand or spread apart the distraction members 144 (FIG. 7B). For example, a distal end of the housing 146 may engage a proximal end of the distraction members 144 to prevent proximal movement of the distraction members 144.

Proximal relative movement of the actuator 148 and spacers 142 can be effected by rotation of the knob 145, for example in a clockwise direction. The threaded engagement between the knob 145 and the actuator shaft 148 (which may or may not rotate) causes the shaft 148 to move axially, pulling the spacers 142 axially to separate the distraction members 144. Reverse rotation of the knob 145 pushes the shaft 148 and spacers 142 distally and out of contact with the inclined inner surfaces 150 of the distraction members 144, allowing the distraction members 144 to contract to the unexpanded configuration of FIG. 7A. As with the prior embodiment, this relative movement relationship is linear in the sense that a certain amount of rotation of the knob 145 results in certain amount spreading or contracting (i.e., change in height dimension) of the distraction members 144 and/or the adjustable sizing paddle.

It is within the scope of the present disclosure to make any of a number of variations to the sizing device 140 of FIGS. 7A and 7B, including one or more of the variations described above with respect to the embodiments of FIGS. 2-6B. For example, the rotary actuator controller 145 may be replaced by an actuator controller that moves differently, such as by sliding or translating in a direction generally parallel to the movement of the actuator 148, or the distraction members 144 may be provided with non-parallel outer contact surfaces or there may be only one movable distraction member 144. In another variation, the spacers 142 may be differently shaped, rather than being substantially identical, as shown in FIGS. 7A and 7B. In yet another variation, the inclination of the spacers and the inner surfaces of the distraction members is reversed, in which case distal movement of the actuator and the spacers causes an increase in the height dimension of the distraction members and/or the adjustable sizing paddle.

According to another aspect of the present disclosure, a sizing or distraction device may be provided that allows the distal paddle or distraction assembly to be able to reach and distract areas not as accessible to a straight sizing device (e.g., a contra-lateral side of a disc space in relation to the device entry point into the disc space). In such embodiments, the adjustable sizing paddle or distraction members can be curved to access other regions of the work space not easily accessed by straight paddles or distraction members. For example, FIGS. 8a and 8b show, in more detail, an exemplary design for a distraction/sizing device generally at 200 that may be curved to varying degrees of curvature.

Figure 8A:
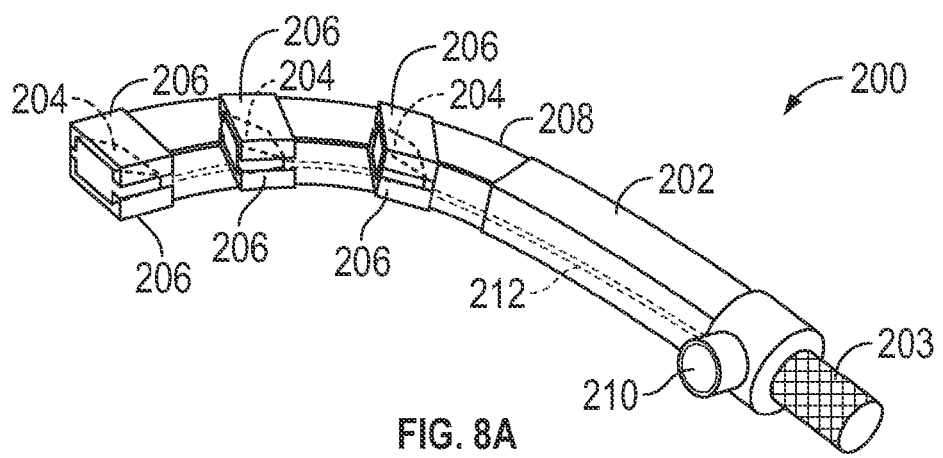
FIG. 8A is a perspective view of another embodiment of a sizing device according to an aspect of the present disclosure, shown in a first or unexpanded configuration.
Figure 8B:
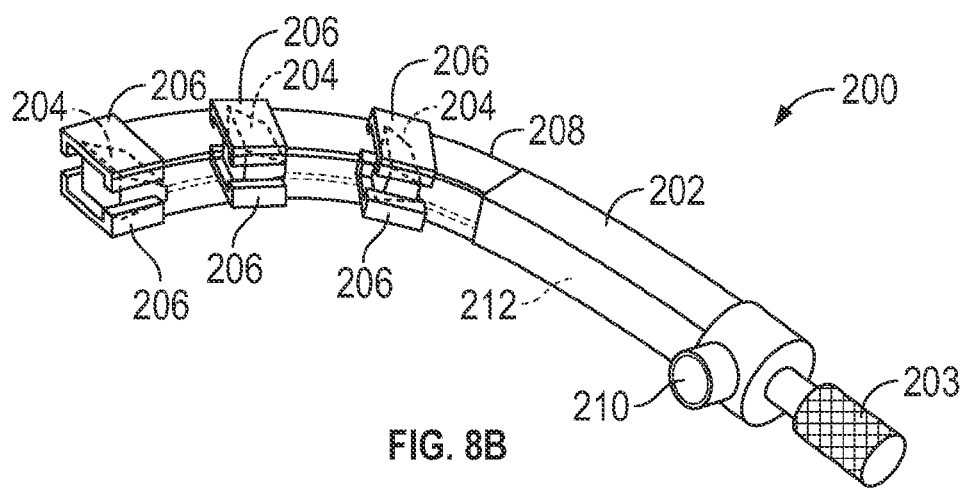
FIG. 8B is a perspective view of the sizing device of FIG. 8A, shown in a second or expanded configuration.

The sizing device 200 of FIGS. 8A and 8B includes, as illustrated, a proximal cannulated housing 202 and an actuator controller, such as a rotary knob or handle 203, rotatably mounted at one end of the housing 202 for moving one or more distal wedges or wedge-shaped spacers 204 in a manner similar to that described with respect to FIGS. 7A and 7B. As in the embodiment of FIGS. 7A and 7B, the spacers 204 may be associated with the actuator controller 203 by an actuator shaft (as in the embodiment of FIGS. 7A-7B) or any other suitable actuator structure.

Figure 9:
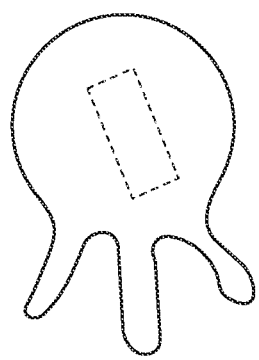
FIG. 9 is a diagrammatic view of the deployment of a sizing device having a generally linear configuration into an intervertebral disc space.
Figure 10:
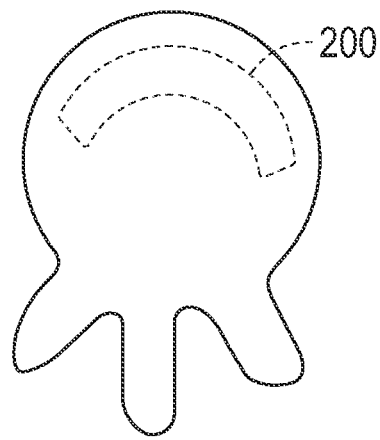
FIG. 10 is a diagrammatic view of the deployment of a sizing device having a generally non-linear configuration into an intervertebral disc space.
Figure 11:
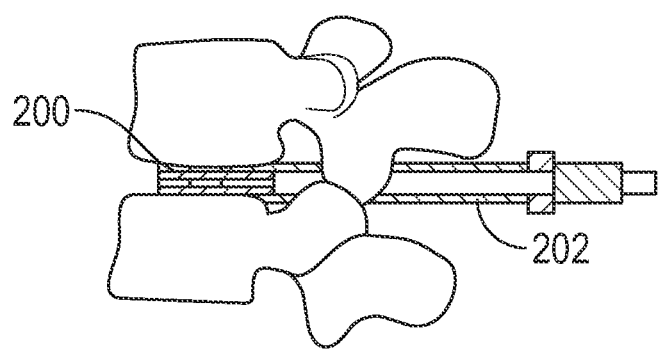
FIG. 11 is a side elevational view of the deployment of a sizing device having a generally non-linear configuration into an intervertebral disc space.

The distal end of the sizing device 200 further includes one or more pairs of opposing distraction panels or members 206 that combine to define an adjustable sizing paddle. In the illustrated embodiment, three pairs of distraction members 206 are spaced along an axial rail or guide 208 and are configured as a series of laterally articulating regions or portions that allow for lateral curvature of the distal end of the sizing device 200. Curvature may be effected in various ways, but as illustrated, the sizing device 200 includes a curvature controller or second actuator controller, such as a thumb screw or knob 210 mounted to the side of the housing 202. Rotation of the knob 210 tensions or releases a pull wire 212 that extends through the housing 202 to the distal-most articulating portion, where it may be fixed or otherwise operably engaged. By tensioning the pull wire 212, the distal end portion, including the distracting members 206 and spacers 204, can be articulated to form a generally curved distal portion or adjustable sizing paddle. As illustrated in FIGS. 9-11, this allows for distraction of surfaces of a work space (shown as a vertebral disc space) that is more difficult to reach with a straight distraction portion or sizing paddle.

To distract two surfaces of a work space with the device of FIGS. 8A and 8B, at least the distal end portion of the device 200 is inserted into the work space, such as through an access cannula in the case of a surgical work space. The side actuator knob 210 may be rotated as or after the distal portion is inserted into the work space to exert tension on the pull wire 212 and curve the adjustable sizing paddle to the desired extent. The distraction members 206 are preferably in the retracted or collapsed low profile condition of FIG. 8A when inserted. The distraction members 206 are separated by moving the actuator controller 203 (i.e., by rotating the actuator knob in the illustrated embodiment), which moves the spacers 204 against engaging inclined inner surfaces of the distraction members 206 to lift and separate the distraction members 206 to the extent desired to size or distract the opposing surfaces of the work space (FIG. 8B). Significantly, the spacers 204 can be of different sizes and/or can have different angles to provide varying amounts of distraction or distraction force along the device. After distraction/sizing, the actuator knob 203 is rotated in the reverse direction and the spacers 204 move in the opposite direction to allow the distraction members 206 to retract to the initial low profile insertion position of FIG. 8A, at which time the device 200 may be withdrawn from the work space.

Although described using wedge-shaped spacers, the device 200 may employ other means for expanding (separating) and contracting (collapsing) the distraction members, such as the scissor linkage pair arrangement described earlier, or any other suitable displacement converter arrangement, which preferably provides a linear actuation relation between the degree of movement of the actuator controller 203 and the change in separation distance between the distraction members 206 (i.e., the height dimension). It is also within the scope of the present disclosure to make any of a number of other variations to the sizing device 200 of FIGS. 8A and 8B, including one or more of the variations described above with respect to the embodiments of FIGS. 2-7B. For example, the rotary actuator controller 203 may be replaced by an actuator controller that moves differently, such as by sliding or translating in a direction generally parallel to the movement of the actuator, or the distraction members 206 may be provided with non-parallel outer contact surfaces or there may be only one movable distraction member 206. In another variation, the spacers 204 may be differently shaped, rather than being substantially identical, as shown in FIGS. 8A and 8B. In yet another variation, the inclination of the spacers and the inner surfaces of the distraction members is reversed, in which case distal movement of the actuator and the spacers causes an increase in the height dimension of the distraction members and/or the adjustable sizing paddle.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A sizing device for measuring and/or adjusting the spacing between two opposing surfaces, comprising:
   at least one distraction member
      cooperatively associated with a distal end of the sizing device,
      adapted for at least partial insertion into a space between two surfaces, and
      movable between a first configuration for insertion into the space in which the at least one distraction member has a height dimension and a second configuration in which the at least one distraction member has a larger height dimension for measuring and/or adjusting the spacing between the two surfaces;
   an actuator associated with the at least one distraction member and movable to change the height dimension of the at least one distraction member; and
   an actuator controller associated with the actuator by a linkage assembly and configured for rotational movement to move the actuator, wherein
   the linkage assembly includes first and second linkage fixtures connected to the actuator by pivotal links,
   at least one linkage fixture is movable toward and away from the other linkage fixture in a direction substantially perpendicular to a direction of movement of the actuator upon rotation of the actuator controller,
   a portion of the linkage assembly is configured to rotate upon rotation of the actuator controller,
   a second portion of the linkage assembly is configured to non-rotatably move upon rotation of the actuator controller, and
   the amount of movement of the actuator controller is generally linearly related to the change of the height dimension of the at least one distraction member.

2. The sizing device of claim 1, wherein the height dimension of the at least one distraction member is infinitely adjustable between the height dimensions of the first and second configurations.

3. The sizing device of claim 1, further comprising a second distraction member, wherein the distraction members are movable toward and away from each other in response to movement of the actuator.

4. The sizing device of claim 3, wherein the actuator is movable between the distraction members.

5. The sizing device of claim 3, further comprising a force measurement assembly associated with the actuator for measuring a reaction force applied by the two surfaces on the distraction members.

6. The sizing device of claim 5, further comprising a clutch assembly associated with the force measurement assembly, wherein the clutch assembly is configured to slip to limit the movement of the distraction members if the reaction force measured by the force measurement assembly reaches and/or exceeds a pre-selected force level.

7. The sizing device of claim 6, wherein the clutch assembly is configured to slip at the same reaction force, regardless of the height dimension of the distraction members.

8. The sizing device of claim 1, wherein the actuator is configured for translational movement.

9. The sizing device of claim 1, wherein the actuator controller is rotatable about an axis oriented at an angle with respect to a direction of movement of the actuator.

10. The sizing device of claim 1, wherein the actuator controller is rotatable about an axis substantially perpendicular to a direction of movement of the actuator.

11. The sizing device of claim 1, further comprising a readout indicator for displaying a value indicative of the height dimension of the at least one distraction member.

12. The sizing device of claim 1, wherein
   the at least one distraction member is movable in a plane between the first and second configurations,
   the actuator controller is rotated about an axis that is parallel to said plane to move the actuator, and the amount of rotation of the actuator controller is generally linearly related to the change of the height dimension of the at least one distraction member.

13. The sizing device of claim 1, wherein the actuator controller is configured to be removed and replaced by a second actuator controller that is differently movable than the actuator controller.

14. The sizing device of claim 1, wherein the second portion of the linkage assembly is configured for translational movement upon rotation of the actuator controller.

15. The sizing device of claim 1, wherein the second portion of the linkage assembly is configured for pivotal movement upon rotation of the actuator controller.

16. A sizing device for measuring and/or adjusting the spacing between two opposing surfaces, comprising:
    at least one distraction member
        cooperatively associated with a distal end of the sizing device,
        adapted for at least partial insertion into a space between two surfaces, and
        movable between a first configuration for insertion into the space in which the at least one distraction member has a height dimension and a second configuration in which the at least one distraction member has a larger height dimension for measuring and/or adjusting the spacing between the two surfaces;
    an actuator associated with the at least one distraction member and movable to change the height dimension of the at least one distraction member; and
    an actuator controller associated with the actuator by a linkage assembly and configured for rotational movement to move the actuator, wherein
    the linkage assembly includes first and second linkage fixtures connected to the actuator by pivotal links,
    at least one linkage fixture is movable toward and away from the other linkage fixture upon rotation of the actuator controller, with movement of said at least one linkage fixture away from the other linkage fixture causes movement of the distraction member from the first configuration to the second configuration,
    a portion of the linkage assembly is configured to rotate upon rotation of the actuator controller,
    a second portion of the linkage assembly is configured to non-rotatably move upon rotation of the actuator controller, and
    the amount of movement of the actuator controller is generally linearly related to the change of the height dimension of the at least one distraction member.

17. The sizing device of claim 16, further comprising a second distraction member, wherein the distraction members are movable toward and away from each other in response to movement of the actuator.

18. The sizing device of claim 17, further comprising a force measurement assembly associated with the actuator for measuring a reaction force applied by the two surfaces on the distraction members.

19. The sizing device of claim 18, further comprising a clutch assembly associated with the force measurement assembly, wherein the clutch assembly is configured to slip to limit the movement of the distraction members if the reaction force measured by the force measurement assembly reaches and/or exceeds a pre-selected force level.

20. A sizing device for measuring and/or adjusting the spacing between two opposing surfaces, comprising:
    at least one distraction member
        cooperatively associated with a distal end of the sizing device,
        adapted for at least partial insertion into a space between two surfaces, and
        movable between a first configuration for insertion into the space in which the at least one distraction member has a height dimension and a second configuration in which the at least one distraction member has a larger height dimension for measuring and/or adjusting the spacing between the two surfaces;
    an actuator associated with the at least one distraction member and movable to change the height dimension of the at least one distraction member; and
    an actuator controller associated with the actuator by a linkage assembly and configured for rotational movement to move the actuator, wherein
    the linkage assembly includes first and second linkage fixtures connected to the actuator by pivotal links,
    at least one linkage fixture is movable toward and away from the other linkage fixture upon rotation of the actuator controller, with movement of said at least one linkage fixture toward the other linkage fixture causes movement of the distraction member from the second configuration to the first configuration,
    a portion of the linkage assembly is configured to rotate upon rotation of the actuator controller,
    a second portion of the linkage assembly is configured to non-rotatably move upon rotation of the actuator controller, and
    the amount of movement of the actuator controller is generally linearly related to the change of the height dimension of the at least one distraction member.

* * * * *